United States Patent
Armacost et al.

(10) Patent No.: US 8,771,367 B2
(45) Date of Patent: Jul. 8, 2014

(54) SELF CENTERING, ANTI-SEIZING ACETABULAR LINER

(71) Applicants: John M Armacost, Warsaw, IN (US); James A Caywood, Fort Wayne, IN (US); Ryan C Keefer, Warsaw, IN (US)

(72) Inventors: John M Armacost, Warsaw, IN (US); James A Caywood, Fort Wayne, IN (US); Ryan C Keefer, Warsaw, IN (US)

(73) Assignee: Depuy Synthes Products, LLC, Raynham, MA (US)

( * ) Notice: Subject to any disclaimer, the term of this patent is extended or adjusted under 35 U.S.C. 154(b) by 0 days.

(21) Appl. No.: 13/623,158

(22) Filed: Sep. 20, 2012

(65) Prior Publication Data
US 2013/0085576 A1    Apr. 4, 2013

Related U.S. Application Data

(60) Provisional application No. 61/541,135, filed on Sep. 30, 2011.

(51) Int. Cl.
*A61F 2/34* (2006.01)
*A61F 2/30* (2006.01)

(52) U.S. Cl.
CPC ......... *A61F 2/34* (2013.01); *A61F 2002/30332* (2013.01); *A61F 2002/3411* (2013.01)
USPC .................................... 623/22.28; 623/22.24

(58) Field of Classification Search
None
See application file for complete search history.

(56) References Cited

U.S. PATENT DOCUMENTS

| | | | |
|---|---|---|---|
| 6,610,097 B2* | 8/2003 | Serbousek et al. | 623/22.24 |
| 6,622,097 B2 | 9/2003 | Hunter et al. | |
| 7,326,253 B2* | 2/2008 | Synder et al. | 623/22.4 |
| 7,955,395 B2* | 6/2011 | Shea et al. | 623/22.28 |
| 8,366,780 B2* | 2/2013 | Klawitter et al. | 623/18.11 |
| 2002/0068980 A1 | 6/2002 | Serbousek et al. | |
| 2003/0105529 A1 | 6/2003 | Synder et al. | |
| 2004/0225671 A1 | 11/2004 | Carroll et al. | |
| 2007/0106392 A1* | 5/2007 | Servidio et al. | 623/22.28 |
| 2007/0203583 A1 | 8/2007 | Slone | |
| 2011/0009975 A1* | 1/2011 | Allen et al. | 623/22.24 |
| 2011/0190901 A1* | 8/2011 | Weissberg et al. | 623/22.24 |
| 2012/0143343 A1* | 6/2012 | Meridew et al. | 623/22.15 |

FOREIGN PATENT DOCUMENTS

| | | |
|---|---|---|
| EP | 1493406 A2 | 1/2005 |
| EP | 1728489 A1 | 12/2006 |
| EP | 1806112 A1 | 11/2007 |

(Continued)

OTHER PUBLICATIONS

European Patent Office, Partial Search Report, corresponding Patent Application No. 12186729.5-2310, Jan. 23, 2013. (6 pages).

(Continued)

*Primary Examiner* — David H Willse
*Assistant Examiner* — Javier Blanco

(57) ABSTRACT

A liner adapted for insertion into an acetabular shell for use in hip arthroplasty. The liner includes a concave inner surface adapted to engage a femoral head. The liner also includes an outer surface adapted to engage the acetabular shell and a rim that extends between the inner surface and the outer surface. The outer surface includes a locking section extending from the rim, a composite-curved section extending from the locking section at a first transition point, and a dome section extending from the composite-curved section, wherein at the first transition point, the composite-curved section is tangential to the locking section.

4 Claims, 9 Drawing Sheets

(56) References Cited

FOREIGN PATENT DOCUMENTS

| | | | |
|---|---|---|---|
| FR | 2877563 | A1 | 5/2006 |
| WO | WO 9719656 | A1 | 6/1997 |
| WO | WO 0074604 | A1 | 12/2000 |

OTHER PUBLICATIONS

European Patent Office, Search Report, corresponding Patent Application No. 12186729.5-1654, Apr. 4, 2013. (10 pages).

\* cited by examiner

SELF CENTERING, ANTI-SEIZING ACETABULAR LINER

TECHNICAL FIELD

The present invention relates generally to an implant for use in orthopaedic surgery.

BACKGROUND OF THE INVENTION

A joint within the human body forms a juncture between two or more bones or other skeletal parts. The ankle, hip, knee, shoulder, elbow and wrist are just a few examples of the multitude of joints found within the body. As should be apparent from the above list of examples of joints, many of the joints permit relative motion between the bones. For example, the motion of sliding, gliding, hinge or ball and socket movements may be had by a joint. For example, the ankle permits a hinge movement, the knee allows for a combination of gliding and hinge movements and the shoulder and hip permit movement through a ball and socket arrangement.

The joints in the body are stressed or can be damaged in a variety of ways. For example, the gradual wear and tear is imposed on the joints through the continuous use of a joint over the years. The joints that permit motion have cartilage positioned between the bones providing lubrication to the motion and also absorbing some of the forces direct to the joint. Over time, the normal use of a joint may wear down the cartilage and bring the moving bones in direct contact with each other. In contrast, in normal use, a trauma to a joint, such as the delivery of a large force, from an accident for, example, an automobile accident, may cause considerable damage to the bones, the cartilage or to other connective tissue such as tendons or ligaments.

Arthropathy, a term referring to a disease of the joint, is another way in which a joint may become damaged. Perhaps the best-known joint disease is arthritis, which is generally referred to as a disease or inflammation of a joint that results in pain, swelling, stiffness, instability, and often deformity.

There are many different forms of arthritis, with osteoarthritis being the most common and resulting from the wear and tear of a cartilage within a joint. Another type of arthritis is osteonecrosis, which is caused by the death of a part of the bone due to loss of blood supply. Other types of arthritis are caused by trauma to the joint while others, such as rheumatoid arthritis, Lupus, and psoriatic arthritis destroy cartilage and are associated with the inflammation of the joint lining.

The hip joint is one of the joints that is commonly afflicted with arthropathy. The hip joint is a ball and socket joint that joins the femur or thighbone with the pelvis. The pelvis has a semispherical socket called the acetabulum for receiving a ball socket head in the femur. Both the head of the femur and the acetabulum are coated with cartilage for allowing the femur to move easily within the pelvis. Other joints commonly afflicted with arthropathy include the spine, knee, shoulder, carpals, metacarpals, and phalanges of the hand. Arthroplasty as opposed to arthropathy commonly refers to the making of an artificial joint. In severe cases of arthritis or other forms of arthropathy, such as when pain is overwhelming or when a joint has a limited range of mobility, a partial or total replacement of the joint within an artificial joint may be justified. The procedure for replacing the joint varies, of course, with the particular joint in question, but in general involves replacing a terminal portion of an afflicted bone with a prosthetic implant and inserting a member to serve as a substitute for the cartilage.

The prosthetic implant is formed of a rigid material that becomes bonded with the bone and provides strength and rigidity to the joint and the cartilage substitute members chosen to provide lubrication to the joint and to absorb some of the compressive forces. Suitable material for the implant include metals, and composite materials such as titanium, cobalt chromium, stainless steel, ceramic and suitable materials for cartilage substitutes include polyethylene. A cement may also be used to secure the prosthetic implant to the host bone.

A total hip replacement, for example, involves removing the ball shaped head of the femur and inserting a stem implant into the center of the bone, which is referred to as the medullary canal, or marrow of the bone. The stem implant may be cemented into the medullary canal or may have a porous coated surface for allowing the bone to heal directly to the implant. The stem implant has a neck and a ball shaped head, which are intended to perform the same functions as a healthy femur's neck and a ball shaped head.

A cup or shell may be positioned directly into the acetabulum. The cup or shell may include a porous coating for promoting bony in-growth to secure the shell to the acetabulum. Alternatively or in addition, the shell may include an opening or a plurality of openings for receiving bone screws to assist in the attachment of the shell to the acetabulum. The cup may be made of a metal, for example, cobalt chromium, stainless steel, or titanium. Alternatively, the cup may be made of a ceramic or of a polyethylene. In some embodiments, the cup directly engages the head. In other embodiments, a liner of some sort is inserted into the cup to articulate against the head. The liner may be made of metal, ceramic, or polyethylene.

Metal and ceramic liners are often locked into the shell via a taper lock, meaning that the shell includes a taper and the liner includes a corresponding taper that fits into the taper of the shell. If properly seated, the shell taper and the liner taper engage one another and lock the liner into the shell. However, during insertion, the conical taper of the liner may become misaligned with the conical taper of the shell, thus preventing the intended surface-to-surface lock of the conical tapers. This is called cross-locking, characterized by a less stable edge or multi-point lock. If a misalignment exists during insertion, there is an increased risk of implant facture and other complications during surgery.

When a liner becomes cross-locked, the surgeon must decide whether to leave the liner in the cross-locked position, try to remove the liner from the shell, or remove the entire implant construct. Leaving a cross-locked liner in the shell presents multiple risks to the patient including: increased wear, disassembly of the implant construct, non-optimal range of motion and implant fracture. Removing the liner from the shell or the entire construct also creates risks and adds complications to the surgery.

Therefore, there is a need for a liner that eliminates or greatly reduces the occurrence of a cross-locked taper junction.

SUMMARY OF THE INVENTION

According to one embodiment of the present invention, a liner is provided that is adapted for insertion into an acetabular shell for use in hip arthroplasty. The liner includes a concave inner surface adapted to engage a femoral head. The liner also includes an outer surface adapted to engage the acetabular shell and a rim that extends between the inner surface and the outer surface. The outer surface includes a locking section extending from the rim, a composite-curved section extending from the locking section at a first transition point, and a dome section extending from the composite-curved section, wherein at the first transition point, the composite-curved section is tangential to the locking section.

In another embodiment, a kit for use in arthroplasty is provided. The kit includes a shell and a liner adapted to be inserted into the shell. The liner includes an inner surface and an outer surface. The inner surface is generally concave and the outer surface is adapted to engage the acetabular shell. The outer surface includes a locking section and a composite-curved section, the composite-curved section including a radial portion and a straight-line tangential portion.

In yet another embodiment of the present invention, a liner is provided. The liner is for use in arthroplasty and includes an inner and an outer surface. The outer surface is adapted to engage an acetabular shell and includes a locking section and a composite-curved section. The composite-curved section extends tangentially from the locking section.

BRIEF DESCRIPTION OF THE DRAWINGS

For a more complete understanding of the present invention and the advantages thereof, reference is now made to the following description taken in connection with the accompanying drawings, in which.

DETAILED DESCRIPTION OF THE DRAWINGS

Embodiments of the present invention and the advantages thereof are best understood by referring to the following descriptions and drawings, wherein like numerals are used for like and corresponding parts of the drawings.

Figure 1:
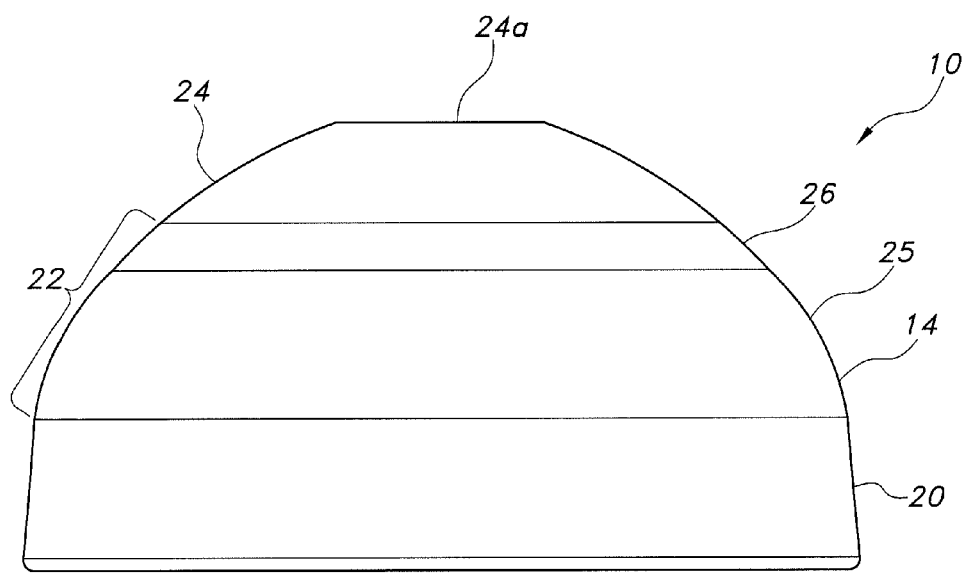
FIG. 1 is a perspective view of a liner according to one embodiment of the present invention.
Figure 2:
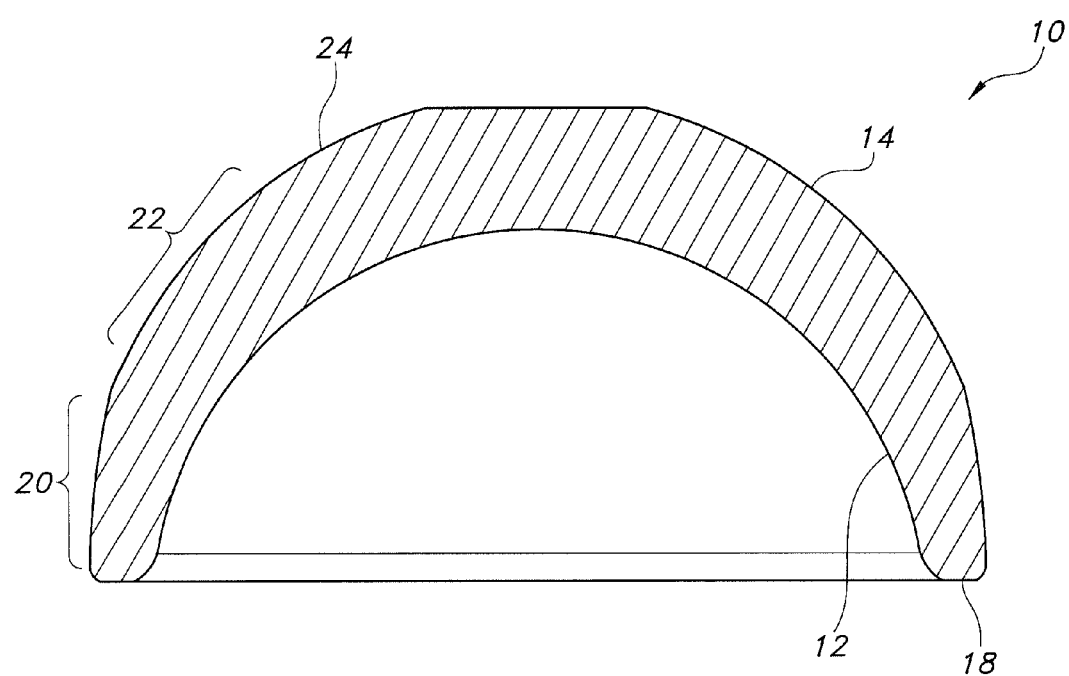
FIG. 2 is a cross-sectional view of the liner of FIG. 1.
Figure 5:
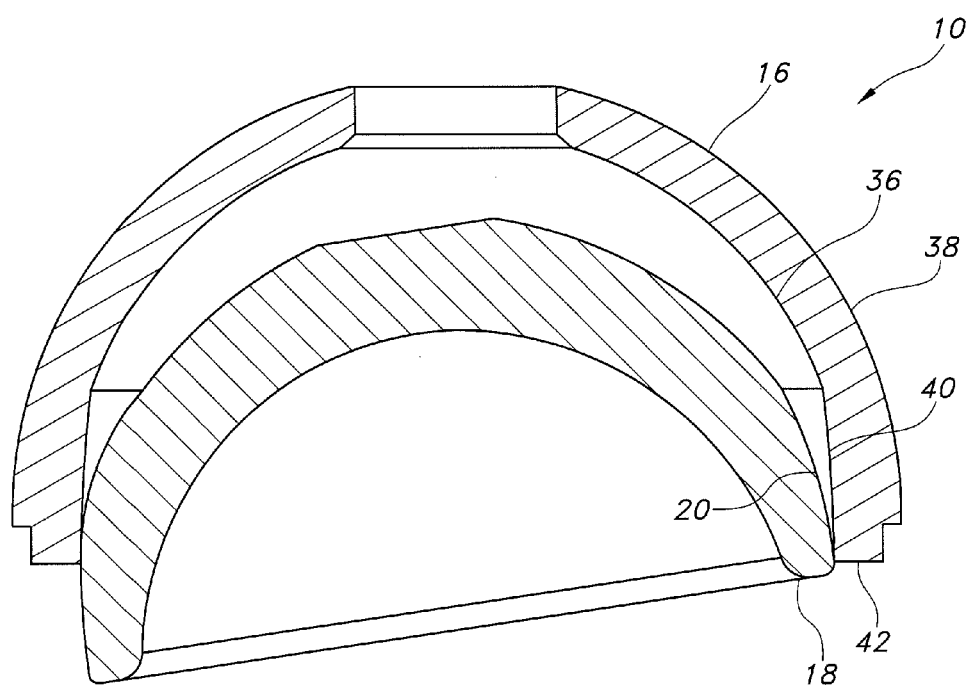
FIG. 5 is a cross-sectional view of the liner of FIG. 1 in conjunction with a shell, with the liner in misalignment.
Figure 6:
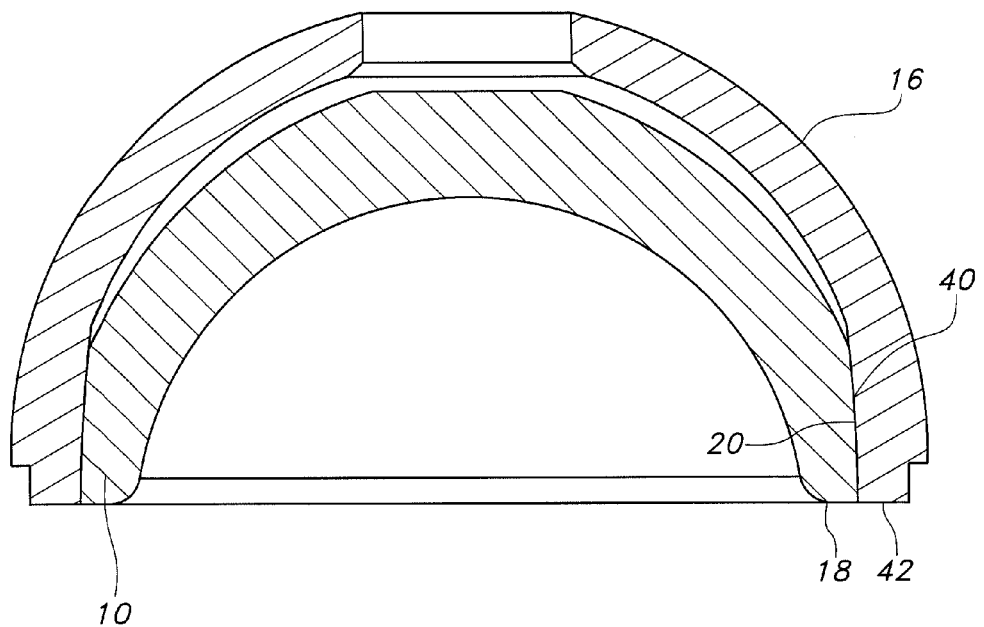
FIG. 6 is a cross-sectional view of the liner of FIG. 1 in conjunction with a shell, with the liner properly seated within the shell.

Turning now to FIGS. 1 and 2, a liner 10 according to one embodiment of the present invention is shown. The liner 10 includes an inner surface (or bearing surface) 12. As shown, the bearing surface 12 in this embodiment is generally concave. The bearing surface 12 is designed to articulate with a femoral head (not shown). The liner 10 also includes an outer surface 14. The outer surface 14 is designed to fit into a shell 16 (FIGS. 5 and 6). The bearing surface 12 and outer surface 14 are coupled to a rim 18 that extends between the bearing surface 12 and the outer surface 14. In other words, the rim 18 is between the bearing surface 12 and the outer surface 14. In this embodiment, the bearing surface 12, outer surface 14, and rim 18 are all made of a singular piece. In other embodiments, these pieces may be modular and locked together.

Still referring to FIGS. 1 and 2, the outer surface 14 will be described in greater detail. The outer surface 14 includes a locking section 20, a composite-curved section 22, and a dome section 24. In this embodiment, the dome section 24 includes a flattened top portion 24a as is common in some prior art liner designs. However, it should be understood that in some liners 10, there may not be a flattened top portion. The locking section 20 extends from the rim 18 and is sized and shaped to engage the shell 16 as will be described in more detail below. In this embodiment, the locking section 20 is a conically tapered wall, but other known locking mechanisms may be used.

Figure 3:
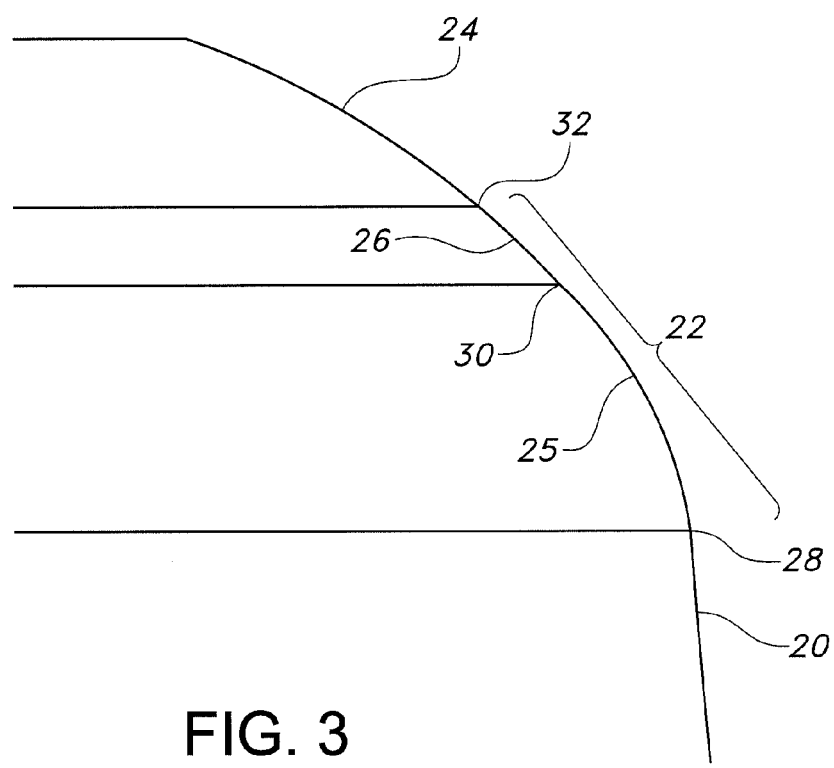
FIG. 3 is an enlarged view of a portion of the liner of FIG. 1.

In the embodiment illustrated in FIGS. 1 and 2, the composite-curved section 22 includes two portions: a radial portion 25 and a tangential portion 26. In the illustrated embodiment, the radial portion is curved and the tangential portion 26 is a straight line. In other embodiments, the tangential portion 26 may also be curved, having a radius that is different from the radius of the radial portion. As shown in FIG. 3, an enlarged view of the liner 10 around the composite-curved section 22, the locking section 20 is tangential to the radial portion 25 at a transition point 28. In other words, the radial portion 25 extends tangentially from the locking section 20. Because the radial portion 25 is tangential to the locking section 20, there are no edges and there is continuity between the locking section 20 and the radial portion 25. The radial portion 25 is curved having a circular radius that is tangential to the locking section 20, thereby defining its center.

As shown in FIG. 2, the composite-curved section 22 extends from the locking section 20 starting at the point where the locking section 20 ends. In some embodiments, there is no dome section 24, and the composite-curved section 22 extends all the way to the top of the liner 10.

Returning now to FIG. 3, the radial portion 25 tangentially blends into the tangential portion 26 at a transition point 30. In other words, the tangential portion 26 extends tangentially from the radial portion 25 at the transition point 30. The radial portion 25 is tangential with the tangential portion at point 30, so that no edge or sharp point exists on the liner 10. The tangential portion 26 is a straight line that is also tangential with the dome section 24 at a transition point 32. In other words, the tangential portion 26 is a straight line that is tangential to both the radial portion 25 and the dome section 24. By having the tangential portion 26 be tangential to both these two curved areas 24, 25, there are no edges or corners, reducing rough surfaces. The tangential portion 26 is a straight line in the embodiment illustrated in FIGS. 1-3. In other embodiments, the tangential portion 26 may be curved. In yet other embodiments, as described further in FIG. 7, there may not be a tangential portion. The composite-curved section 22 may only include the radial portion 25.

Figure 4:
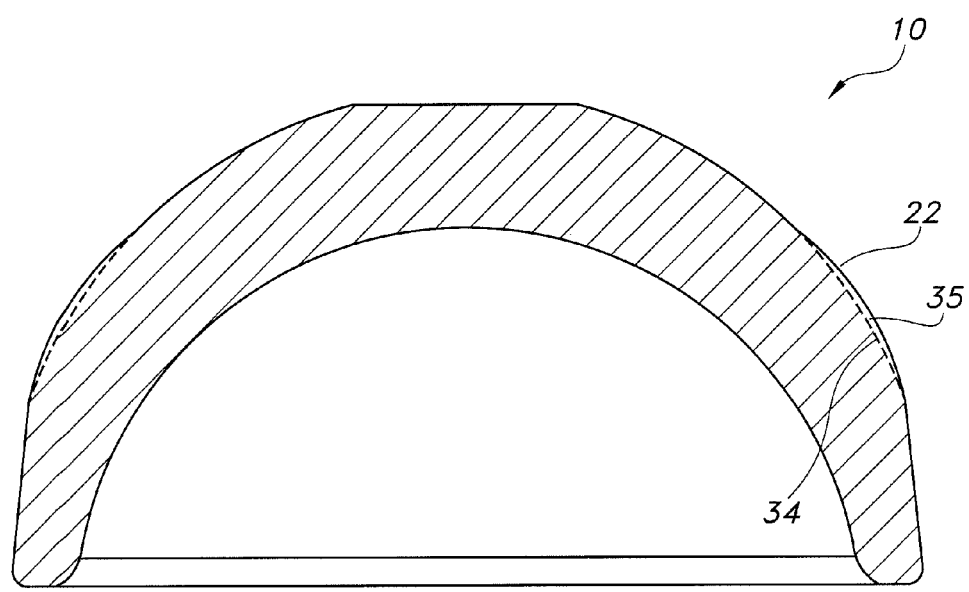
FIG. 4 is a cross-sectional view of the liner of FIG. 1 super-imposed over a prior art liner.

Looking at FIG. 4, the liner 10 is shown super-imposed over a prior art liner (line 34). As can be seen the composite-curved portion 22 extends outwardly from the corresponding outer portion 34 of the prior art liner. This additional material is represented by shaded portion 35 in FIG. 4. The additional material in the liner 10 reduces the amount of clearance between the liner 10 and the shell 16 when the two pieces are assembled as will be further illustrated in FIGS. 5 and 6 below.

In some embodiments, the curvature of the radial portion 25 is determined by maximizing the radius of the radial portion 25, while still being able to create a tangential portion 26 that is tangential to both the radial portion 25 and the dome section 24. However, in other embodiments, other parameters may determine the curvature of the radial portion 25.

Turning now to FIGS. 5 and 6, the liner 10 is shown inserted into a shell 16. The shell 16 includes an inner surface 36 and an outer surface 38. The outer surface 38 is designed to fit in an acetabulum (not shown). The inner surface 36 includes a locking section 40 that is designed to mate with the locking section 20 of the liner 10. In this embodiment, the locking section 40 is a taper that mates with the tapered locking section 20 of the liner 10. In this embodiment, the locking sections 40, 20 of the shell 16 and liner 10 are self-locking tapers as is known in the art.

When the liner 10 is first introduced into the shell 16, if the locking sections 20 and 40 are misaligned as shown in FIG. 5, the liner 10 "floats" within the shell 16 and is not flush within the shell 16. In other words, the rim 18 of the liner 10 is not flush with a rim 42 of the shell 16. This allows the user to ensure alignment between the locking sections 20, 40 of the liner 10 and shell 16 before seating. As described above, the composite-curved portion 22 includes added material (shaded portion 35 from FIG. 4), reducing the clearance between the liner 10 and the shell 16. Thus, unless the locking sections 20 and 40 of the shell 16 and liner 10 are aligned, the composite-curved portion 22 abuts the shell to keep the liner from dropping into place. Once the liner 10 and shell 16 are aligned, the locking sections 20, 40 engage and the locking section 20 of the liner 10 is in full taper contact with the locking section 40 of the shell 16 and the liner 10 and shell 16 can be fully seated as shown in FIG. 6. If a liner 10 is fully seated in the shell 16, the rim 18 of the liner 10 is flush with the rim 42 of the shell 16.

Figure 7:
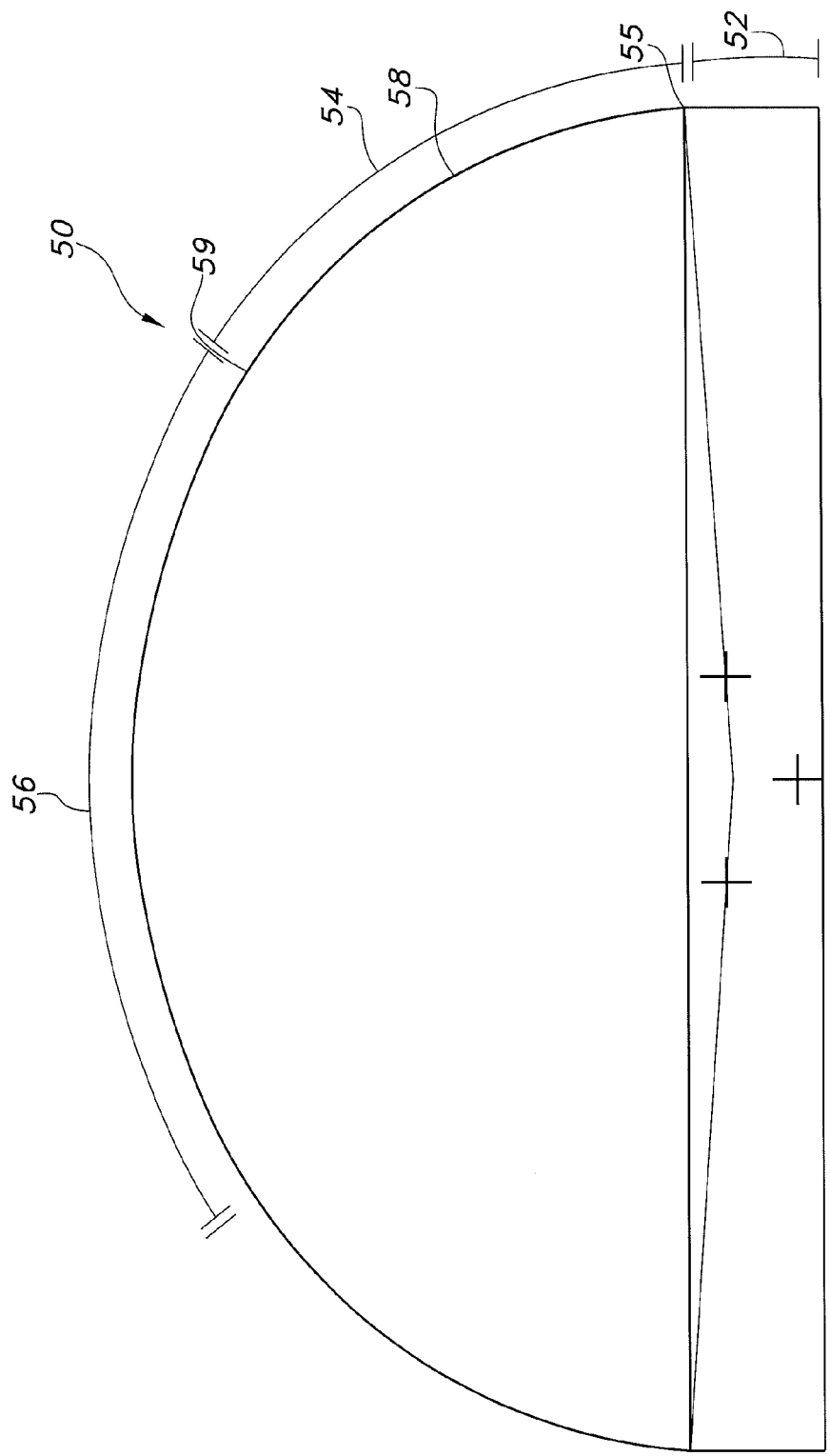
FIG. 7. is a perspective view of a liner according to another embodiment of the present invention.

FIG. 7 illustrates another embodiment of the present invention. The embodiment includes a liner 50. The liner 50 includes a locking section 52, a composite-curved section 54, and a dome section 56. In this embodiment, the composite-curved section 54 comprises a single curved portion 58. In other words, there is not a straight-line tangential section as described in the embodiment of FIGS. 1-6 above. The curved portion 58 of the composite-curved section 54 extends from a point 55 where the locking section ends. In some embodiments, there is no dome section 56 and the composite-curved section 54 extends to the top of the liner 10. In other embodiments where there is a dome section 56, the composite-curved section 54 blends into the dome section 56 at a point 59. In this embodiment, the curved portion 58 extends tangentially from the locking section 52 and from the dome section 56.

Figure 8:
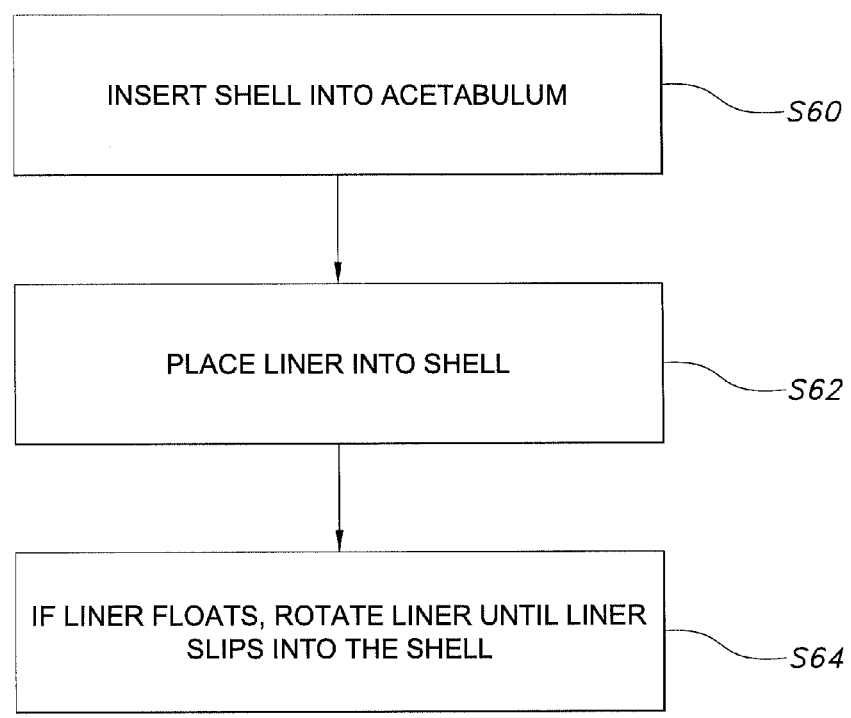
FIG. 8 is a flow-chart depicting a method of using a liner and a shell according to one embodiment of the present invention.

Turning now to FIG. 8, a method of using one embodiment of the present invention is described. At step s60, the shell 16 is inserted into the acetabulum (not shown). The liner 10, 50 is placed into the shell (s62). If the liner 10, 50 is floating, then the user rotates the liner 10, 50 (step s64) until it slips into the shell 16 as shown in FIG. 6. In some embodiments, step s60 may be done after the liner 10, 50 is inserted into the shell. In other words, the liner/shell combination could be either assembled in the operating room or it could come pre-assembled as in a monoblock shell with having the liner and shell assembled together beforehand. The user may be the surgeon assembling the shell and liner during the surgery, or the user could be someone who preassembles the device and then the shell and liner assembly is delivered to the surgery preassembled.

Figure 9:
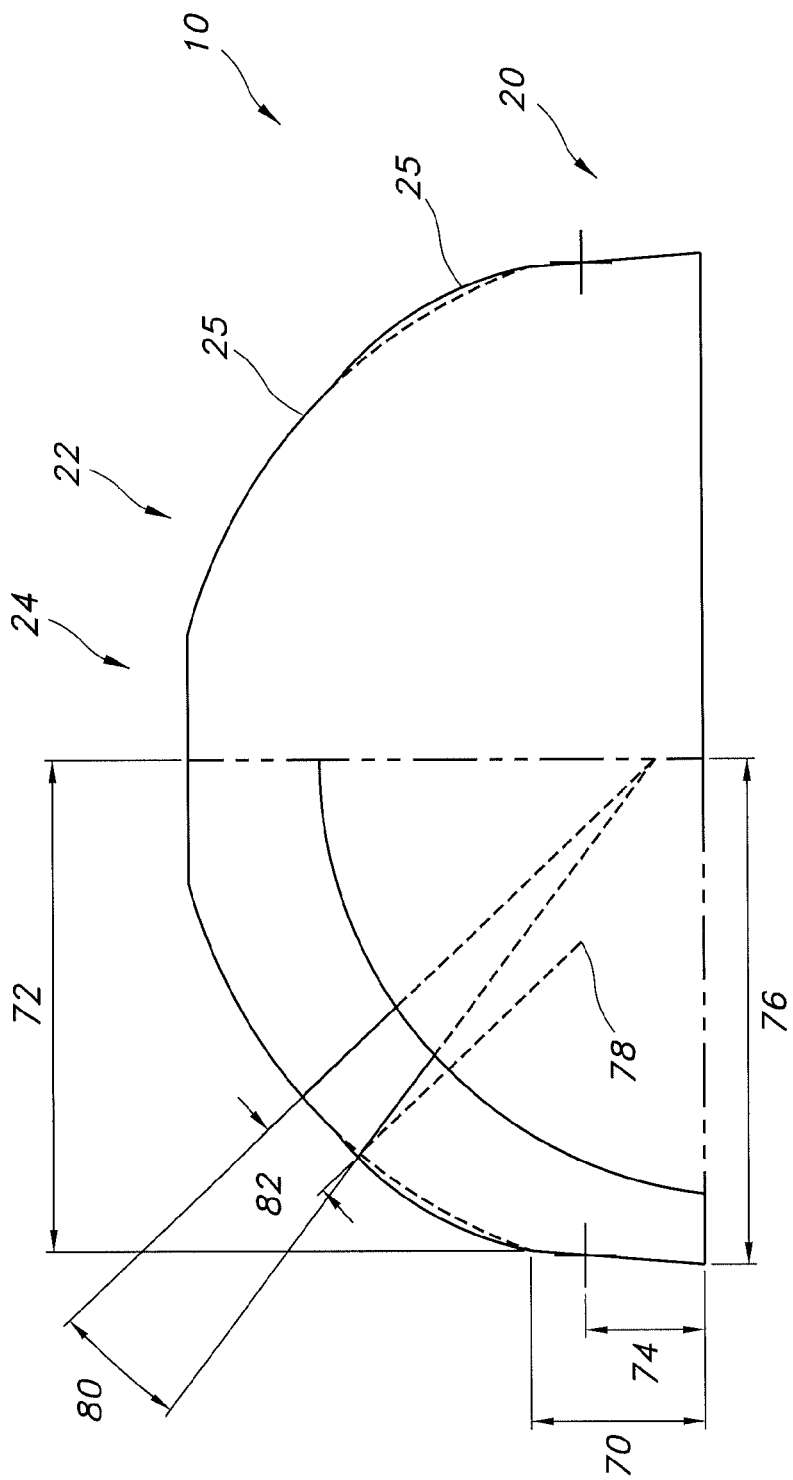
FIG. 9 is a partial cross-sectional view of the liner of FIG. 1, indicating various dimensions between the regions according to one embodiment of the present invention.

Turning now to FIG. 9, a partial cross-sectional view of the liner 10 is illustrated. In this embodiment, the liner 10 has the outer surface 14, which includes the locking section 20, the composite-curved section 22, and the dome section 24. The composite-curved section 22 includes two portions: the radial portion 25 and the tangential portion 26. FIG. 9 illustrates one embodiment setting forth the various dimensions of these sections and regions. As shown, the locking section 20 has a height 70 is between about 0.250 and 0.300 inches. The locking section 20 has a taper gage diameter 72 between about 1.2 inches and 2.0 inches and a taper gage location 74 between about 0.190 inches and 2.20 inches. The locking section 20 also has a taper angle 76 between 5 and 6 degrees.

The radial portion 25 has a blend radius 78 of between 0.250 and 0.750 inches. The tangential flat portion extends for an angle 80 between about 9.0 and 10.0 degrees and has a length 82 between about 0.10 and 0.15 inches.

While the invention is susceptible to various modifications and alternative forms, a specific embodiment thereof has been shown by way of example in the drawings and will herein be described in detail. It should be understood, however, that there is no intent to limit the invention to the particular form disclosed, but on the contrary, the intention is to cover all modifications, equivalents, and alternatives falling within the spirit and scope of the invention as defined by the appended claims.

The invention claimed is:

1. A kit for use in hip arthroplasty comprising:
    an acetabular shell; and
    an acetabular liner adapted for insertion into said acetabular shell, the liner comprising:
        a concave inner surface adapted to engage a femoral head;
        an outer surface adapted to engage the acetabular shell; and
        a rim extending between the inner surface and the outer surface, wherein the outer surface includes a locking section extending from the rim, a composite-curved section extending from the locking section at a first transition point, and a dome section extending from the composite-curved section, wherein at the first transition point, the composite-curved section is tangential to the locking section,
    wherein the composite-curved section includes a curved radial portion and a straight-line tangential portion, wherein the radial portion extends from the locking section at the first transition point, and wherein the tangential portion extends from the radial portion at a second transition point,
    wherein the tangential portion is tangential to the radial portion at the second transition point,
    wherein the dome section extends from the tangential portion at a third transition point, wherein the tangential portion is tangential to the dome section at the third transition point, and
    wherein there is continuity between the locking section and the radial portion, and continuity between the tangential portion and the dome section, so that no edge or sharp point exists on the outer surface of the acetabular liner.

2. The kit of claim 1, wherein the shell includes a locking section adapted to engage the locking section of the liner.

3. The kit of claim 2, wherein the shell locking section and the liner locking section are self-locking tapers.

4. The kit of claim 1, wherein the dome section includes a flattened top portion.

* * * * *